US012613235B2

(12) United States Patent
Jungblut et al.

(10) Patent No.: US 12,613,235 B2
(45) Date of Patent: Apr. 28, 2026

(54) METHOD AND KIT FOR CHARACTERIZING DOPAMINERGIC PROGENITOR CELLS OBTAINED BY DIFFERENTIATING PLURIPOTENT STEM CELLS

(71) Applicant: Miltenyi Biotec B.V. & Co. KG, Bergisch Gladbach (DE)

(72) Inventors: Melanie Jungblut, Bergisch Gladbach (DE); Andreas Bosio, Cologne (DE); Sebastian Knobel, Cologne (DE); Agnete Kirkeby, Hellerup (DK); Malin Parmar, Lund (SE)

(73) Assignee: MILTENYI BIOTEC B.V. & CO. KG, Bergisch Gladbach (DE)

( * ) Notice: Subject to any disclaimer, the term of this patent is extended or adjusted under 35 U.S.C. 154(b) by 62 days.

(21) Appl. No.: 18/443,732

(22) Filed: Feb. 16, 2024

(65) Prior Publication Data

US 2024/0248076 A1     Jul. 25, 2024

Related U.S. Application Data

(63) Continuation of application No. 16/632,229, filed as application No. PCT/EP2018/069197 on Jul. 16, 2018, now Pat. No. 12,013,388.

(30) Foreign Application Priority Data

Jul. 17, 2017     (EP) ..................................... 17181588

(51) Int. Cl.
*G01N 33/58*        (2006.01)
*G01N 33/50*        (2006.01)
(52) U.S. Cl.
CPC ......... *G01N 33/5005* (2013.01); *G01N 33/58* (2013.01)

(58) Field of Classification Search
CPC ........................... G01N 33/5005; G01N 33/58
See application file for complete search history.

(56) References Cited

U.S. PATENT DOCUMENTS

| | | | |
|---|---|---|---|
| 10,072,245 | B2 | 9/2018 | Bosio et al. |
| 2016/0348070 | A1* | 12/2016 | Kirkeby ................. A61P 25/28 |

FOREIGN PATENT DOCUMENTS

| | | |
|---|---|---|
| WO | 2010096496 A2 | 8/2010 |
| WO | 2016196661 A1 | 12/2016 |

OTHER PUBLICATIONS

Barker et al., "Fetal Dopaminergic Transplantation Trials and the Future of Neural Grafting in Parkinson's Disease", The Lancet Neurology, vol. 12, No. 1, Jan. 1, 2013, pp. 84-91.

(Continued)

*Primary Examiner* — David W Berke-Schlessel
*Assistant Examiner* — Trent R Clarke
(74) *Attorney, Agent, or Firm* — Kilpatrick Townsend & Stockton LI.F

(57)        ABSTRACT

This disclosure provides a method and kit for analyzing compositions of human floorplate mesencephalic dopaminergic (mesDA) progenitor cells that are obtained, for example, by differentiating embryonic stem cells. The mesDA progenitors are characterized using the positive markers FOXA2. OTX2, and optionally NKX2. 1. in combination with the negative markers OCT3/4, and optionally PAX6, and SOXI. Cells with an appropriate protein expression profile have therapeutic potential for restoring the function of dopaminergic neurons in conditions such as Parkinson's Disease.

18 Claims, 7 Drawing Sheets

(56) References Cited

OTHER PUBLICATIONS

Grealish et al., "Human ESC-Derived Dopamine Neurons Show Similar Preclinical Efficacy and Potency to Fetal Neurons when Grafted in a Rat Model of Parkinson's Disease", Cell Stem Cell, vol. 15, No. 5, Nov. 6, 2014, pp. 653-665.

Kefalopoulou et al., "Long-Term Clinical Outcome of Fetal Cell Transplantation for Parkinson Disease Two Case Reports", JAMA Neurology, vol. 71, No. 1, Jan. 2014, pp. 83-87.

Kirkeby et al., "Building Authentic Midbrain Dopaminergic Neurons From Stem Cells—Lessons From Development", Translational Neuroscience, vol. 3, No. 4, Nov. 20, 2012, pp. 314-319.

Kirkeby et al., "Generating Regionalized Neuronal Cells From Pluripotency, a Step-by-Step Protocol", Frontiers in Cellular Neuroscience, vol. 6, No. 64, Jan. 3, 2013, pp. 1-4.

Kirkeby et al., "Generation of Regionally Specified Neural Progenitors and Functional Neurons From Human Embryonic Stem Cells Under Defined Conditions", Cell Reports, vol. 1, No. 6, Jun. 28, 2012, pp. 703-714.

Kirkeby et al., "Predictive Markers Guide Differentiation to Improve Graft Outcome in Clinical Translation of hESC-Based Therapy for Parkinson's Disease", Cell Stem Cell, vol. 20, No. 1, Jan. 5, 2017, pp. 1-14.

Kriks et al., "Dopamine Neurons Derived From Human ES Cells Efficiently Engraft in Animal Models of Parkinson's Disease", Nature, vol. 480, No. 7378, Nov. 6, 2011, pp. 547-551.

Ladewig et al., "Small Molecules Enable Highly Efficient Neuronal Conversion of Human Fibroblasts", Nature Methods, vol. 9, No. 6, Jun. 2012, pp. 1-6.

Nakatani et al., "Lmx1a and Lmx1b Cooperate With Foxa2 to Coordinate the Specification of Dopaminergic Neurons and Control of Floor Plate Cell Differentiation in the Developing Mesencephalon", Developmental Biology, vol. 339, No. 1, Mar. 1, 2010, pp. 101-113.

Application No. PCT/EP2018/069197, International Search Report and Written Opinion, Mailed on Sep. 7, 2018, 8 pages.

Puelles et al., "Otx2 Regulates the Extent, Identity and Fate of Neuronal Progenitor Domains in the Ventral Midbrain", Development, vol. 131, No. 9, Mar. 31, 2004, pp. 2037-2048.

\* cited by examiner

METHOD AND KIT FOR CHARACTERIZING DOPAMINERGIC PROGENITOR CELLS OBTAINED BY DIFFERENTIATING PLURIPOTENT STEM CELLS

RELATED APPLICATIONS

This application claims benefit and is a continuation of application Ser. No. 16/632,229 filed Jan. 17, 2020 (pending), which is a 371 application and claims the benefit of PCT Application No. PCT/EP2018/069197, filed Jul. 16, 2018 (expired), which claims benefit of EP patent application Ser. No. 17/181,588.9, filed Jul. 17, 2017. The aforesaid priority applications are hereby incorporated herein by reference in their entireties for all purposes.

FIELD OF THE INVENTION

The work leading to this invention has received funding from the European Union Seventh Framework Programme FP7/2007-2013 under grant agreement no. 602278.

The present invention relates to a method for analyzing the protein expression profile on a single cell level of human floorplate mesencephalic dopaminergic progenitor cells.

BACKGROUND OF THE INVENTION

Midbrain Dopaminergic (DA) neurons secrete the neurotransmitter dopamine and play a central role in different brain functions, like cognition, memory processing, motor control, and motion.

They are found in three distinct nuclei, the substantia nigra pars compacta (A9 group), the ventral tegmental area (A10 group) and the retrorubral field (A8 group). The cell bodies of the A9 group in the substantia nigra pars compacta (SNpc) of the midbrain, innervate the caudate putamen, the dorsalateral striatum and form the nigrostriatal pathway, which regulates motor function by the controlled release of dopamine from projecting dopaminergic neurons.

Degeneration of the A9 dopaminergic neurons in the substantia nigra is mainly responsible for dysfunction of the dopamine system and for several motor features described as the disorder Parkinson's disease (PD). Although PD involves also degeneration of other neuronal subtypes, loss of substantia nigra pars compacta dopaminergic neurons is mainly responsible for PD symptoms and has become a primary target for cell replacement therapy.

During fetal development progenitors of these DA neurons are formed in the ventral neural tube of the developing mesencephalon. Progenitor cells from the so-called floor plate region are characterized by expression of the transcription factors FOXA2, LMX1A and OTX2. These cells give rise to DA SNpc neurons (A9 group) and to DA ventral tegmental area neurons (A10 group). It was shown that fetal cells dissected form the fetal mesencephalon and transplanted to the striatum of Parkinson patients could functionally re-innervate the striatum and restore the functions of dopaminergic neurons (Barker, 2013; Kefalopoulou, 2014). But, the limited availability of fetal DA progenitors and ethical as well as logistical concerns using this tissue emphasized the necessity of an alternative cell source.

In the past years, factors that are critical for successful differentiation of pluripotent stem cells (PSCs) or induced pluripotent stem cells (iPSCs) into ventral mesencephalic (mes) dopaminergic (DA) progenitor cells were identified and led to various protocols for in-vitro differentiation protocols for generation of therapeutically relevant mesDA neurons (Kriks, 2011; Kirkeby, 2012; Kirkeby, 2013; Grealish, 2014; Kirkeby 2017), which is the most promising cell population for clinical use in the context of PD as it resembles the more complex composition of the ventral mesencephalon of post coitum week 6-7.5 human embryos (EP3061809).

Different studies suggest that mesDA progenitor cells differentiated from embryonic stem cells have the same features as cells derived from the human fetal ventral mesencephalon in terms of i) subtype-specific maturation, ii) integration and projection capacity in a rat Parkinson model, iii) regulated DA release and iv) functional reversion of Parkinson symptoms (Grealish, 2014; Kirkeby, 2012).

Protocols are based on dual SMAD inhibition for neural conversion and regionalization by chemical inhibition of glycogen synthase kinase 3 (GSK3) to induce WNT signaling for caudalised patterning into midbrain fates and activation of sonic hedgehog (SHH) signaling for patterning into ventral fates (Kirkeby, 2013).

Although protocols are optimized for generation of dopaminergic neuron progenitor cells, differences in the manufactured cell lots cannot be avoided. It is known that in vitro differentiated cell cultures may contain cells with unwanted cell fate or differentiation stages as the differentiation process is a highly sophisticated and sensitive procedure where the experimental outcome can be influenced by slight variations (e.g. user dependent handling variations, cell density, variations in starting cell composition such as cell line, passage number and culture conditions prior to initiation of differentiation and growth factor potency).

Therefore, one need within the generation of GMP-grade PSC/iPSC derived mesDA neurons is the set-up of a reliable in vitro assay for comprehensive cell product characterization, that allows to determine the identity and purity of the cell lot. Furthermore, the assay must correlate with the cells' potential to engraft and to mature to midbrain dopaminergic neurons, as well as reveal a potential tumorigenicity.

Usually mesencephalic floor plate markers, like LMX1A, FOXA2 and OTX2 are used to confirm the identity of the cells prior to grafting. Recently, Kirkeby et al., identified a set of in vitro markers that allows prediction of successful cell grafting by qRT-PCR (Kirkeby et al., 2017). In addition to LMX1A, FOXA2 and OTX2, predictive markers for a successful grafting results were EN1, ETV5, CNPY1, PAX8, and SPRY1. Furthermore, diencephalic domain markers, as EPHA3, FEZF1, and WNT7B were associated with a negatively correlated graft outcome. However, expression was analyzed on the bulk of cells on the mRNA level. This has several shortcomings. Firstly, it is well known that the mRNA expression level of a gene reflects only its potential to be expressed or present as a protein. Based on a multitude of posttranscriptional regulatory mechanisms, posttranslational modifications and differing stability and turnover of proteins and mRNAs, the conversion of an mRNA to an actual protein can or cannot happen and if it happens it can result in a multitude of different, slightly varying forms of a given protein. Moreover, while the mRNA of a gene might not be detected at a given moment, the corresponding protein can still be present for weeks or even moths. Therefore, it is not possible to irrevocably predict the presence of a certain form of a protein by detecting the corresponding mRNA neither positively nor negatively. Of importance, with the exemption of regulatory RNAs and ribozymes, only a protein and not its corresponding mRNA exerts a function influencing the status of a cell and their environment. Secondly, measurements on a bulk of cells do not reflect the true status of a single cell but rather generate levelled results which might even do not exist in a single cell. But as only a proportion of cells in a given mixture might be the cells of interest or danger the bulk analysis does not have the sensitivity and discriminatory power to allow for a true and quantitative description of different phenotypes of cells in a cell mixture. In addition, methods using PCR based techniques are time-consuming and prone to contamination.

In summary, there is a need for a method that allows the quantitative readout on a protein level of a single cell and is predictive for a successful cell processing and engraftment of floorplate mesDA progenitor cells after transplantation to a subject.

BRIEF SUMMARY OF THE INVENTION

The invention describes a new user friendly, standardized method for protein profiling of floorplate mesDA progenitor cells on the single cell level, that can also be used under GMP conditions. Unexpectedly, we found a combination of markers on the protein level that allows for a clear description of the cellular phenotype. Antigen binding molecules such as antibody-fluorochrome conjugates specific for positive and negative floorplate mesDA progenitor cell markers are used e.g. in a flow cytometry assay that allows for the first time a single cell, quantitative, standardized protein profiling of differentiated floorplate mesDA progenitor cells within approximately 2.5 hours for identification of the cell product's identity.

The set consists of antigen binding molecules, e.g. monoclonal antibody clones that are specific for some or all positive and negative markers of mesDA neurons as disclosed herein (positive markers: FOXA2, OTX2, CD47, NKX2.1; negative markers: OCT3/4, PAX6, SOX1, NKX6.1, KI-67). Percentages of cells being positive or negative for some or all of these cell markers depict a clear picture of the cellular phenotype and purity.

We further found that the marker NKX6.1, which is expressed in the basal plate of the midbrain as well as in the hindbrain of the developing embryo is a surprisingly efficient marker for detecting the presence of hindbrain progenitor fates in differentiated stem cell populations. Therefore, NKX6.1 serves as a negative marker to discriminate lateral midbrain and hindbrain cells from midbrain floor plate-patterned cells. Furthermore, surprisingly, we found that the Marker NKX2.1 is expressed differently when assessed on protein level by flow cytometry compared to PCR. While NKX2.1 mRNA is absent in the floor plate midbrain dopaminergic neurons we have seen that there is still a substantial percentage of NKX2.1positive cells after conversion to human mesDA progenitor cells. The quantification ofNKX2.1 on a protein level can thus monitor potential batch-to-batch variations in cultures of floorplate midbrain progenitors.

In summary, we show for the first time that the quantification and combination of markers and the respective percentage as disclosed herein allow for qualification of in-vitro generated floorplate mesDA progenitor cells prior to cell administration to patients suffering from PD in a cell replacement therapy:

FOXA2 (80-100% (preferentially 90-100%),
OTX2 (80-100%, preferentially 90-100%),
PAX6 (below 10%, preferentially below 5%),
NKX6.1 (below 10%, preferentially below 5%),
Optionally NKX2.1 (5-90%, preferentially 5-70%)

Optionally OCT3/4 (below 0.1%), if the cells are generated from OCT3/4 positive cells This combination can be extended to the at least one (or all) of the following three markers:
KI-67 (10-90%),
IAP (80-100%, preferentially 90-100%),
SOX1 (below 10%, preferentially below 5%).

The depicted protocol follows an adherent differentiation process.

Depending on the used cell line the protocol can be modified, for example addition of Y-27632 instead of thiazovivin and addition of Y-27632 at day 1 as well as day 11.

Figure 3:
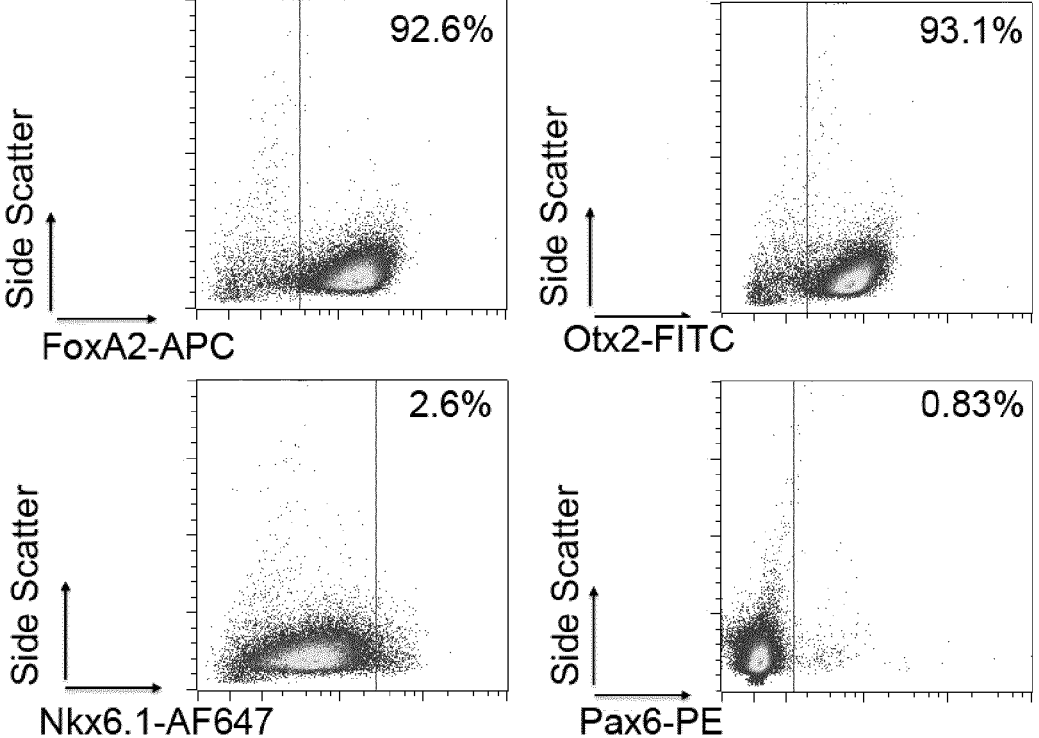
Figure 4:
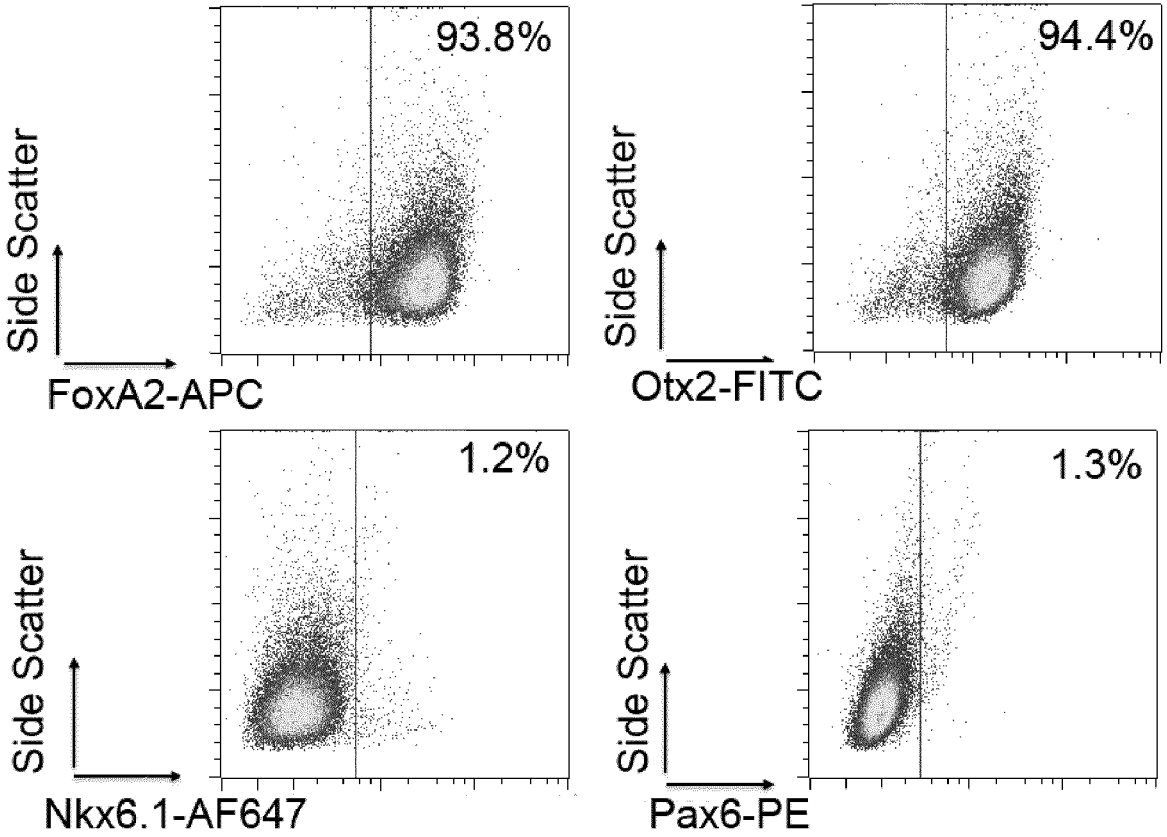
Figure 5:
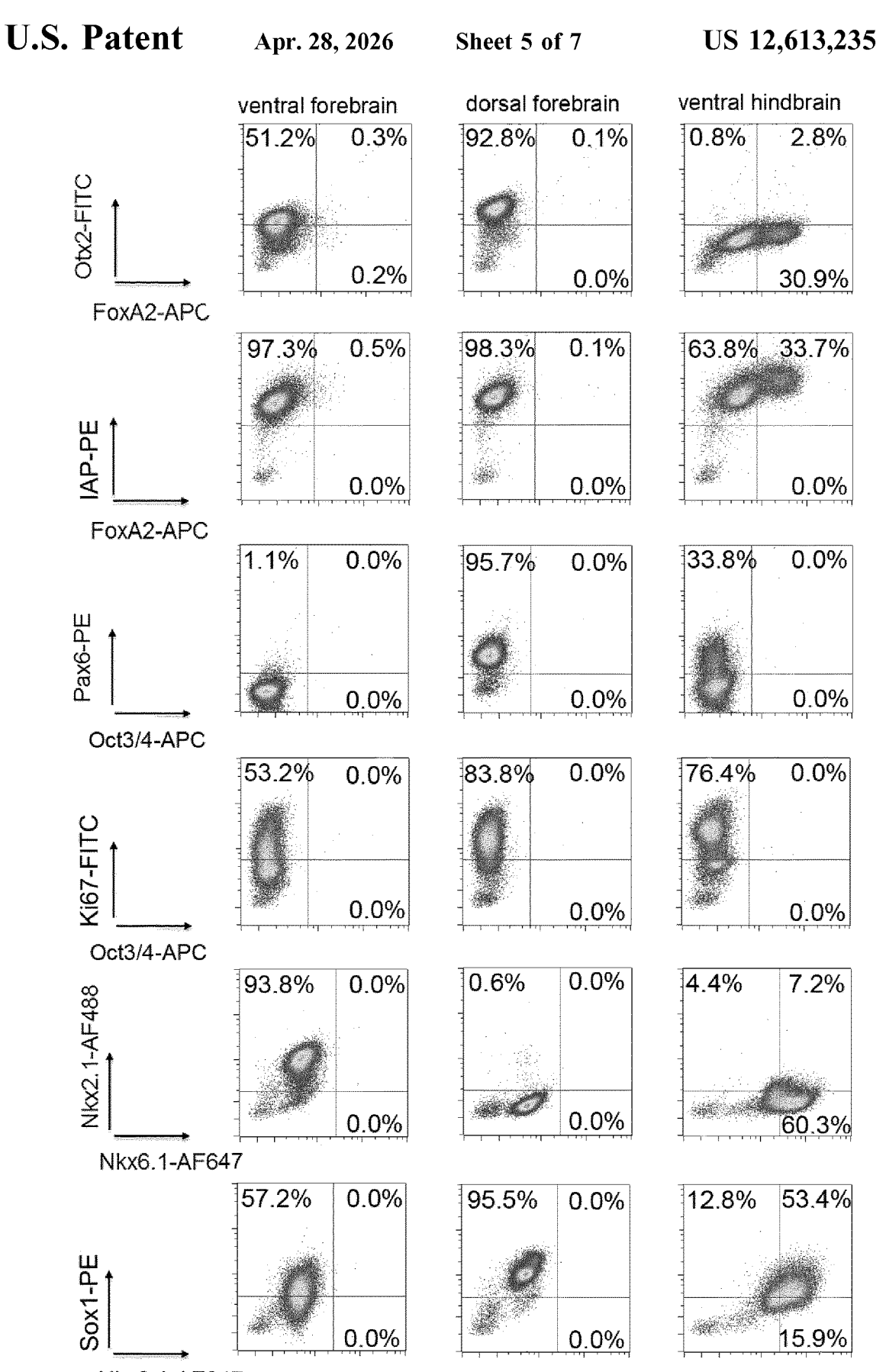
Figure 6:
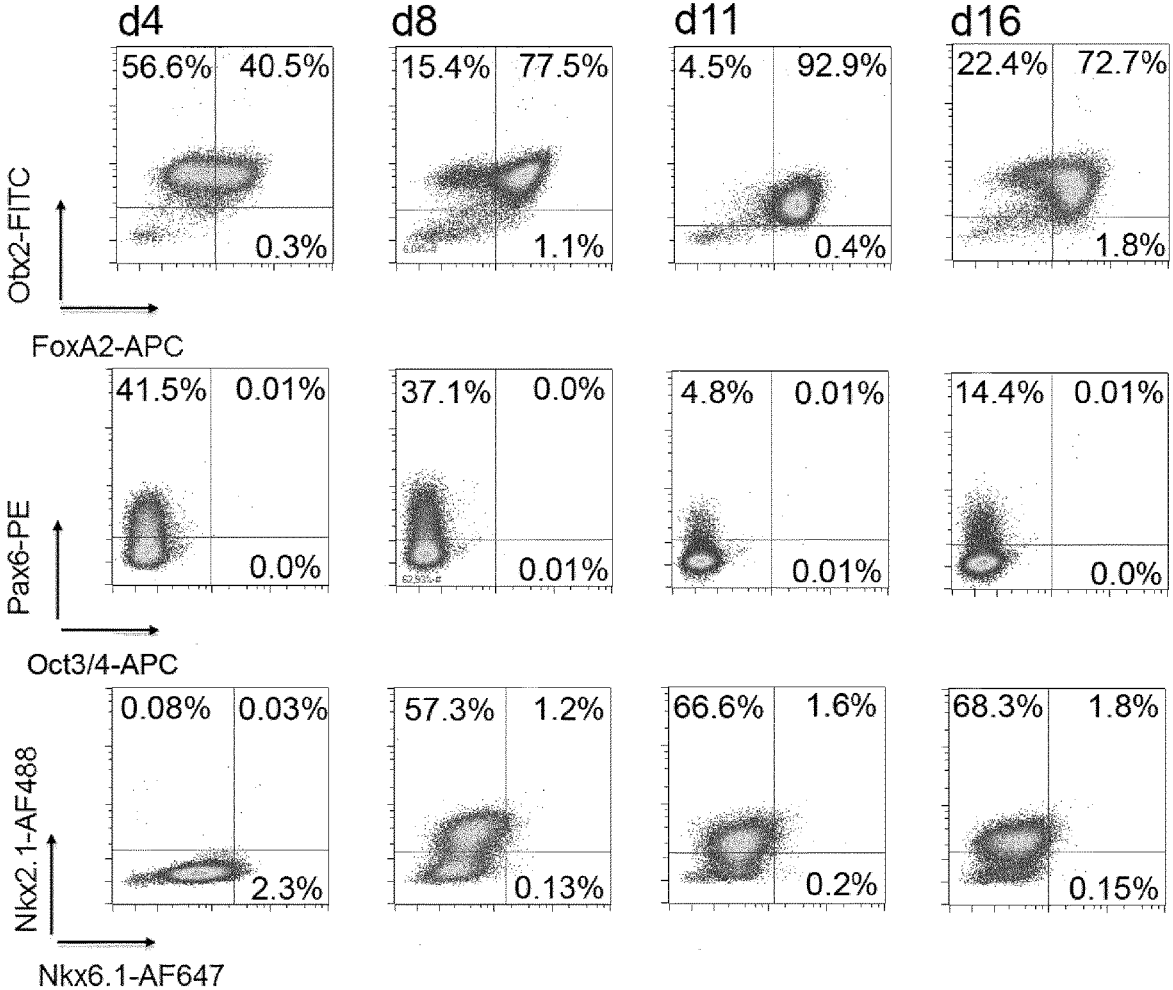

FIG. 3
Flow cytometry analysis of FOXA2, OTX2, NKX6.1, and PAX6 expression of human embryonic stem cells differentiated to floorplate mesDA progenitor cells FIG. 4
Flow cytometry analysis of FOXA2, OTX2, NKX6.1, and PAX6 expression of induced pluripotent stem cells differentiated to floorplate mesDA progenitor cells FIG. 5
Flow cytometry analysis of FOXA2, OTX2, NKX6.1, PAX6, OCT3/4, NKX2.1, IAP, KI-67, and SOX1 expression of pluripotent stem cell derived neural progenitor cultures patterned towards ventral forebrain, dorsal forebrain or ventral hindbrain cells after 16 days of differentiation FIG. 6
Flow cytometry analysis of FOXA2, OTX2, NKX6.1, PAX6, OCT3/4, and NKX2.1 expression after 4, 8, 11, and 16 days of differentiation in pluripotent stem cell cultures differentiated towards floorplate mesDA cells.

Figure 7:
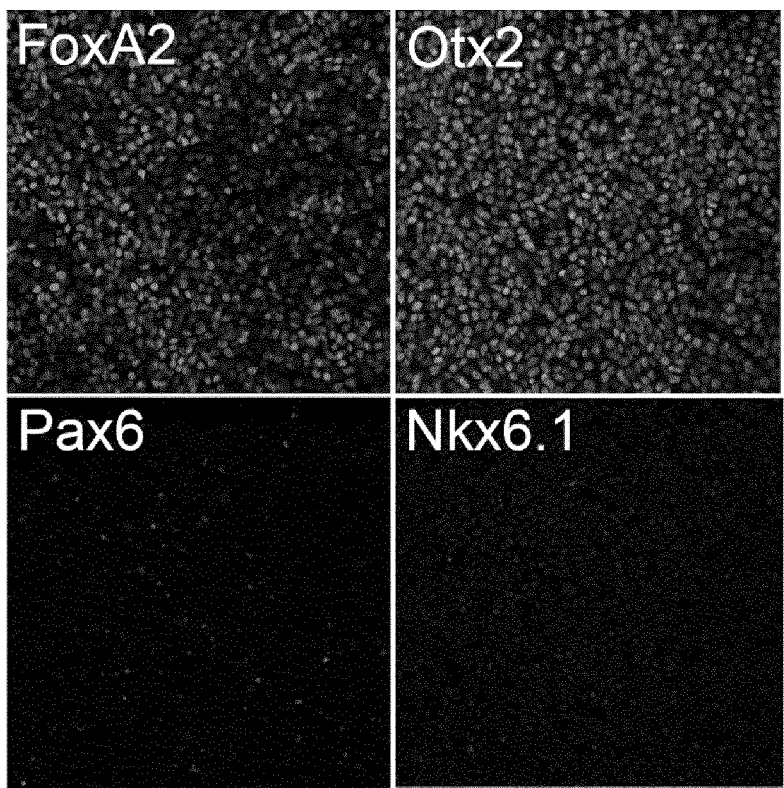

FIG. 7
Immunocytochemical analysis of FOXA2, OTX2, NKX6.1, and PAX6 expression of floorplate mesDA progenitor cells after 11 days of differentiation.

DETAILED DESCRIPTION OF THE INVENTION

The present invention discloses cell markers that can be used for identification of human floorplate mesDA progenitor cells in a cell composition or a sample thereof comprising said cells and possibly other cells by determining the expression profile of the cells with regard to said cell markers as disclosed herein.

In a first aspect the present invention provides an in-vitro method for analyzing a cell composition comprising human floorplate mesDA progenitor cells, the method comprising a) contacting the cells of said cell composition or the cells of a sample thereof with antigen binding molecules specific for the antigens FOXA2, OTX2, PAX6, and NKX6.1, thereby labeling the cells of said cell composition or of said sample b) Determining the percentage of said cells that are labelled with said antigen binding molecules for each of said antigens, and wherein the cells of said cell composition qualify as human floorplate mesDA progenitor cells if the protein expression profile of said cells is:

80-100%, preferentially 90-100% of said cells are positive for FOXA2, 80-100%, preferentially 90-100% of said cells are positive for OTX2, Less than 10%, preferentially less than 5% of said cells are positive for PAX6, and Less than 10%, preferentially less than 5% of said cells are positive for NKX6.1.

Said antigen binding molecules may be conjugated to fluorophores.

The cells of said cell composition or of said sample may be treated with a fixative and a detergent before contacting with said antigen binding molecules as the antigens are transcription factors, therefore the cells of said cell composition or of said sample (step a) may be fixed and permeabilized cells.

The contacting of the cells of said cell composition or of said sample with fluorophore conjugated antigen binding molecules specific for the antigens FOXA2, OTX2, PAX6, and NKX6.1 may be performed consecutively, e.g. firstly a fluorophore conjugated antigen binding molecule specific for FOXA2 may be contacted with the cells of said cell composition or of a sample thereof and subsequently the percentage of said cells may be determined that are labelled with said antigen binding molecule specific for FOXA2, followed by the next fluorophore conjugated antigen binding molecule specific for the next marker as disclosed herein and so on. The antigen binding molecule specific for the first antigen may be removed from the cells of said cell composition or a sample thereof before the second antigen binding molecule specific for the second antigen in contacted with the cells of said cell composition or a sample thereof and so on. Alternatively, the cell composition or a sample thereof provided in step a) of the method is sub-divided into several sub-samples and each antigen binding molecule specific for one of the markers as disclosed herein is contacted with the cells of a single sub-sample. Alternatively, the same cell composition or sample thereof provided in step a) or the sub-samples of the method is used simultaneously for some or all antigen binding molecules specific for the markers as disclosed herein when the antigen binding molecules used are conjugated to distinct detection moieties such as fluorophores that allow for parallel detection of the labeled cells.

Said method, wherein in step a) the cells of said cell composition or of said sample thereof are additionally contacted with an antigen binding molecule specific for the antigen OCT3/4 if said cells of said cell composition or of said sample thereof are derived from OCT3/4 positive cells, and wherein in step) said protein expression profile of the cells of said cell composition or of said sample thereof comprises additionally:

Less than 0.1% of the cells of said cell composition or of said sample thereof are positive for OCT3/4.

Said antigen binding molecule specific for the antigen OCT3/4 may be conjugated to a fluorophore.

Said method, wherein in step a) the cells of said cell composition or of said sample thereof are additionally contacted with an antigen binding molecule specific for the antigen NKX2.1, and wherein in step b) said protein expression profile of the cells of said cell composition or of said sample thereof comprises additionally:

5-90%, preferentially 5-70% of the cells of said cell composition or of said sample thereof are positive for NKX2.1.

Said antigen binding molecule specific for the antigen NKX2.1 may be conjugated to a fluorophore.

Said method, wherein in step a) the cells of said cell composition or of said sample thereof are additionally contacted with an antigen binding molecule specific for the antigen KI-67, and wherein in step b) said protein expression profile of the cells of said cell composition or of said sample thereof comprises additionally:

10-90% of the cells of said cell composition or of said sample thereof are positive for KI-67. Said antigen binding molecule specific for the antigen KI-67 may be conjugated to a fluorophore.

Said method, wherein in step a) the cells of said cell composition or of said sample thereof are additionally contacted with an antigen binding molecule specific for the antigen IAP, and wherein in step b) said protein expression profile of the cells of said cell composition or of said sample thereof comprises additionally:

80-100%, preferentially 90-100% of the cells of said cell composition or of said sample thereof are positive for IAP.

Said antigen binding molecule specific for the antigen IAP may be conjugated to a fluorophore.

Said method, wherein in step a) the cells of said cell composition or of said sample thereof are additionally contacted with an antigen binding molecule specific for the antigen SOX1, and wherein in step b) said protein expression profile of the cells of said cell composition or of said sample thereof comprises additionally:

Less than 10%, preferentially less than 1% of the cells of said cell composition or of said sample thereof are positive for SOX1.

Said antigen binding molecule specific for the antigen SOX1 may be conjugated to a fluorophore.

Said method, wherein in step a) the cells of said cell composition or of said sample thereof are additionally contacted with at least one antigen binding molecule specific for an antigen selected from the group consisting of the antigens KI-67, IAP and SOX1, and wherein in step b) said protein expression profile of the cells of said cell composition or of said sample thereof comprises additionally:

10-90% of the cells of said cell composition or of said sample thereof are positive for KI-67 if in step a) an antigen binding molecule specific for KI-67 is used, 80-100%, preferentially 90-100% of the cells of said cell composition or of said sample thereof are positive for IAP if in step a) an antigen binding molecule specific for IAP is used Less than 5%, preferentially less than 1% of the cells of said cell composition or of said sample thereof are positive for SOX1 if in step a) an antigen binding molecule specific for SOX1 is used.

Said antigen binding molecules may be conjugated to fluorophores.

Said method, wherein said determining the percentage of the cells of said cell composition or of said sample thereof that are labelled with said antigen binding molecules for each of said antigens is performed by flow cytometry or immunocytochemistry.

Said method, wherein said cell composition comprising human floorplate mesDA progenitor cells is generated or is in the process of being generated by an in-vitro differentiation process from human cells, which can be converted to human floorplate mesDA progenitor cells.

Said human cells which can be converted into floorplate mesDA progenitor cells may be selected from the group consisting of human iPS cells, human embryonic stem cells or directly reprogrammed human somatic cells.

Said antigen binding molecules may be antibodies or antigen binding fragments thereof.

In another aspect the present invention provides a kit for analyzing the protein profile of human floorplate mesDA progenitor cells comprising antigen binding molecules specific for the antigens FOXA2, OTX2, PAX6, and NKX6.1.

Said kit, wherein said kit additionally comprises an antigen binding molecule specific for the antigen Oct3/4.

Said kit, wherein said kit additionally comprises an antigen binding molecule specific for the antigen NKX2.1.

Said kit, wherein said kit additionally comprises an antigen binding molecule specific for the antigen KI-67.

Said kit, wherein said kit additionally comprises an antigen binding molecule specific for the antigen IAP.

Said kit, wherein said kit additionally comprises an antigen binding molecule specific for the antigen SOX1

Said kit, wherein said kit additionally comprises at least one antigen binding molecule specific for an antigen selected from the group consisting of the antigens for the antigens KI-67, IAP and SOX1.

Said antigen binding molecules may be conjugated to fluorophores.

The generation of human floorplate mesDA progenitor cells from a starting cell composition comprising cells that can be converted into human floorplate mesDA progenitor cells such as pluripotent stem cells are well-known in the art and is disclosed e.g. in Kriks, 2011; Kirkeby, 2012; Kirkeby, 2013; Grealish, 2015; Kirkeby 2017.

DEFINITIONS

Unless defined otherwise, technical and scientific terms used herein have the same meaning as commonly understood by one of ordinary skill in the art to which this invention belongs.

The term "cell composition comprising human floorplate mesDA progenitor cells" refers to the (complete) cell composition or to a sample thereof comprising human floorplate mesDA progenitor cells and other cells, e g. with other neural identities in any ratio.

Said cell composition comprising human floorplate mesDA progenitor cells may be generated or may be in the process of being generated by an in-vitro differentiation process from human cells, which can be converted to human floorplate mesDA progenitor cells.

The human floorplate mesDA progenitor cells of said cell composition may be derived from human cells, which can be converted to human floorplate mesDA progenitor cells, e.g. human iPS cells, human embryonic stem cells or directly reprogrammed human somatic cells using protocols of differentiation or direct reprogramming well-known in the art such as e.g. in Kriks, 2011; Kirkeby, 2012; Ladewig 2012; Kirkeby, 2013; Grealish, 2015; Kirkeby 2017. The present method as disclosed herein may be used to monitor and/or identify the status of the cells during this process of differentiation of the stem cells into cells that qualify as human floorplate mesDA progenitor cells.

The term "analyzing" in the context of analyzing a cell composition comprising human floorplate mesDA progenitor cells means e.g. identifying human floorplate mesDA progenitor cells in a cell composition or sample by determining the expression profile as disclosed herein of cells of said cell composition or said sample.

A sample may be taken from the (complete) cell composition comprising human floorplate mesDA progenitor cells, e.g. one or more aliquots. Then the method as disclosed herein may comprise the step "providing a sample from said cell composition" before the step a).

The term "Determining the percentage of said cells, i.e. the cells of said cell composition or of said sample thereof, labelled with said antigen binding molecules for each of said antigens" as used herein refers to the determination of the amount of cells in the cell composition or in the sample taken from the cell composition that are e.g. fluorescently labelled for a respective antigen, e.g. if in said cell composition or said sample 9 from 10 cells are labelled for the antigen FOXA2, then 90% of the cells of the cell composition or the sample are positive for FOXA2, if in the same cell composition or sample8 from 10 cells are labeled for the antigen OTX2, then 80% of the cells of the same cell composition or sample are also positive for OTX2. It is irrelevant for the determination if some or all cells are double positive for the markers.

The term "qualify as human floorplate mesDA progenitor cells" as used herein refers to ex-vivo cells that are able to functionally re-innervate the striatum and restore the functions of dopaminergic neurons to at least partially revert the Parkinson symptoms after transplantation into a subject suffering from PD.

The term "cell composition comprising human floorplate mesDA progenitor cells is generated or is in the process of being generated by an in-vitro differentiation process from human cells, which can be converted to human floorplate mesDA progenitor cells" refers to cells of a cell population to which a differentiation protocol was or is applied that includes factors critical for successful differentiation into floorplate mesDA progenitor cells. Therefore, the process allows to differentiate pluripotent cells to human floorplate mesDA progenitor cells, but may contain also cells with unwanted cell fate or differentiation stages.

Human cells which can be converted to human floorplate mesDA progenitor cells may be OCT3/4 positive human iPS cells, OCT3/4 positive human embryonic stem cells or OCT3/4 negative directly reprogrammed human somatic cells. Human embryonic stem cells can be isolated from embryos without destruction as disclosed e.g. in WO 03/046141.

The term "pluripotent stem cell" as used herein refers to cells being capable to self-renew and have the potential to differentiate into any of the embryonic germ layers endoderm, mesoderm and ectoderm and cells derived from this. These criteria hold true for embryonic stem cells (ESC) and induced pluripotent stem cells (iPSC). Preferentially these cells are human. Different degrees of pluripotency are known in the art, referred to as "primed state" pluripotent stem cells, "naive state" pluripotent stem cells or "reset stage" pluripotent stem cells.

The term embryonic stem cells (ESCs) as used herein refer to pluripotent stem cells derived from the inner cell mass of a blastocyst at an early-stage before implantation. ESCs are capable to self-renew and have the potential to differentiate into any of the embryonic germ layers endo- derm, mesoderm and ectoderm and cells derived from this. ESCs show expression of the pluripotency marker OCT3/4.

The term "induced pluripotent stem cells (iPSC)" as used herein refers to pluripotent cells generated by conversion of cells of lower potency, i.e. more differentiated cells, typi- cally a somatic cell, to a state of pluripotency, the resulting cells being capable to self-renew and having the potential to differentiate into any of the embryonic germ layers endo- derm, mesoderm and ectoderm and cells derived from this. iPSCs show expression of the pluripotency marker OCT3/4. Reprogramming may be achieved by methods known in the art such as nuclear transfer, cell fusion, or factor induced reprogramming, i.e. induced expression of one or more reprogramming factors, such as but not limited to OCT3/4, SOX2, KLF4, C-MYC, NANOG, LIN28, etc. Reprogram- ming factors may be introduced as nucleic acids, or proteins by viral transduction or by transfection. Different culture conditions and reprogramming factor combinations may result in different degrees of pluripotency, referred to as "primed state" pluripotent stem cells, "naive state" pluripo- tent stem cells or "reset stage" pluripotent stem cells.

The term "human floorplate mesencephalic dopaminergic progenitor cells (mesDA)" as used herein refers to in vitro differentiated cells characterized by expression of FOXA2 (80-100%), OTX2 (80-100%), PAX6 (below 10%), NKX6.1 (below 10%). This composition reflects a high purity of mesDA progenitor cells with a profile similar to the mesDA progenitors present in the ventral mesencephalon of post coitum week 6-7.5 human embryos, and it is the most promising cell population for clinical use in the context of PD treatment.

Cells may be derived in vitro from different starting cell compositions such as but not limited to embryonic stem cells, induced pluripotent stem cells, reprogrammable somatic cells.

The term "differentiation" as used herein refers to cellular differentiation, a term used in developmental biology, and describes the process by which a less specialized cell becomes a more specialized cell type. In vitro, differentia- tion of stem cells can occur spontaneously or is induced intentionally by adding differentiation inducing substances such as specialized cultivation media, cytokines, receptor antagonists or small molecules to the cultivation media.

Also the cultivation matrix, i.e. the coating of the cell culture ware, may be used to bias the differentiation process by providing different proteins or chemical compounds that are in contact with the cells.

The term "marker" as used herein refers to a cell antigen that is specifically expressed by a certain cell type. The markers may be positive selection markers such as FOXA2, IAP, NKX2.1 and OTX2 as disclosed herein or may be negative selection markers such as OCT3/4, PAX6, SOX1, NKX6.1, KI-67 as used herein.

The term "expression" as used herein is defined as the transcription and/or translation of a particular nucleotide sequence driven by its promoter in a cell.

A "protein expression profile" or "protein signature" of the cells of a cell population or of a cell composition or sample thereof indicates which genes are expressed by these cells.

The term "antigen binding molecule conjugated to a fluorophore" as used herein means the coupling or conjugation of the antigen-binding molecule, e.g. an antibody or antigen binding fragment thereof, to a fluorophore. In some cases the conjugation is a direct coupling or binding of the antigen binding molecule to the fluorophore. In other cases the conjugation is an indirect coupling or binding of the antigen binding molecule to a fluorophore, e.g. via biotin and streptavidin. The antigen may be bound the antigen binding molecule (e.g. primary antibody) and a second molecule (e.g. secondary antibody) that has a conjugated fluorophore then may bind to the antigen binding molecule.

Methods for analysis comprise, for example, flow cytom- etry based methods or fluorescence microscopy.

Flow cytometry is a laser-or impedance-based, biophysi- cal technology employed e.g. in cell sorting and biomarker detection by suspending e.g. cells in a stream of fluid and passing them by an electronic detection apparatus. It allows simultaneous multiparametric analysis of the physical and chemical characteristics of up to thousands of particles per second. Fluorescence-activated cell sorting (FACS™) is a specialized type of flow cytometry. It provides a method for sorting a heterogeneous mixture of biological cells into two or more containers, one cell at a time, based upon the specific light scattering and fluorescent characteristics of each cell.

Immunocytochemistry (ICC) is a common laboratory technique that is used to anatomically visualize the local- ization of a specific protein or antigen in cells by use of e.g. a specific primary antibody that binds to it. The primary antibody allows visualization of the protein under a fluo- rescence microscope when it is directly conjugated to a fluorophore or bound by e.g. a secondary antibody that has a conjugated fluorophore. ICC allows to evaluate whether or not cells in a particular sample express the antigen in question.

The term "antigen-binding molecule" as used herein refers to any molecule that binds preferably to or is specific for the desired target molecule of the cell, i.e. the antigen. The term "antigen-binding molecule" comprises e.g. an antibody or antigen binding fragment thereof The term "antibody" as used herein refers to polyclonal or monoclonal antibodies, which can be generated by methods well known to the person skilled in the art. The antibody may be of any species, e.g. murine, rat, sheep, human.

The term "antibody" comprises both intact molecules and antibody fragments (antigen binding fragments), such as Fab, Fab', F(ab')2, Fv and single-chain antibodies. Addition- ally, the term "antigen-binding molecule" includes any mol- ecule other than antibodies or antigen binding fragments thereof that binds preferentially to the desired target mol- ecule of the cell. Suitable molecules include, without limi- tation, oligonucleotides known as aptamers that bind to desired target molecules, carbohydrates, lectins or any other antigen binding protein (e.g. receptor-ligand interaction). The linkage (coupling) between antibody and fluorophore can be covalent or non-covalent. A non-covalent linkage is e.g. via biotin-avidin. Methods for coupling antibodies to fluorophores are well known to the skilled person in the art.

The terms "specifically binds to" or "specific for" with respect to an antigen-binding molecule, e.g. an antibody or antigen binding fragment thereof, refer to an antigen-bind- ing molecule (in case of an antibody or fragment thereof to an antigen-binding domain) which recognizes and binds to a specific antigen in a cell composition or sample as dis- closed herein, but does not substantially recognize or bind other antigens in said cell composition or said sample. An antigen-binding domain of an antibody or fragment thereof that binds specifically to an antigen from one species may bind also to that antigen from another species. This cross-species reactivity is not contrary to the definition of "specific for" as used herein. An antigen-binding domain of an antibody or fragment thereof that specifically binds to an antigen, may also bind substantially to different variants of said antigen (allelic variants, splice variants, isoforms etc.). This cross reactivity is not contrary to the definition of that antigen-binding domain as specific for the antigen.

Forkhead box protein A2 (FOXA2) is a protein that in humans is encoded by the FOXA2 gene.

Homeobox protein OTX2 is a protein that in humans is encoded by the OTX2 gene.

Paired box protein PAX6 is a protein that in humans is encoded by the PAX6 gene.

Homeobox protein NKX6.1 (also NKX6-1) is a protein that in humans is encoded by the NKX6-1 gene.

Oct-3/4 (octamer-binding transcription factor 3/4, also known as Oct-3 or Oct-4) is a protein that in humans is encoded by the POU5F1 gene.

NK2 homeobox 1 (NKX2-1, NKX2.1 or TTF-1) is a protein which in humans is encoded by the NKX2-1 gene.

Antigen KI-67 also known as Ki-67 or MKI67 is a protein that in humans is encoded by the MKI67 gene (antigen identified by monoclonal antibody Anti-Ki-67).

IAP (integrin associated protein) also known as CD47 (Cluster of Differentiation 47) is a transmembrane protein that in humans is encoded by the CD47 gene.

SOX1 is a gene, which encodes a transcription factor in the HMG (high mobility group) DNA binding domain, and functions primarily in neurogenesis.

EMBODIMENTS

In a first embodiment of the invention, a sample or several samples are taken from a cell composition that are expected to comprise human floorplate mesDA progenitor cells. The cells of the cell composition were in-vitro differentiated from human iPS cells to human floorplate mesDA progenitor cells using e.g. the embryoid body (EB) based protocol described in example 1.

For monitoring the differentiation status, said samples are taken from said cell composition at several time-points, e.g. 4, 6, 8, 11, 14, 16, and/or 18 days after starting the differentiation procedure. After fixation and permeabilization, the cells of the samples are contacted with antigen binding molecules conjugated to fluorophores specific for the antigens FOXA2, OTX2, PAX6, and NKX6.1, thereby labeling the cells of said sample. Optionally said sample or samples are also contacted with one, more or all of the following antigen binding molecules conjugated to fluorophores specific for the antigens: OCT3/4, NKX2.1, KI-67, IAP, SOX1.

The protein expression profile of the cells of the sample(s) is/are determined e.g. by flow cytometry.

The cells of the sample or samples that show the following protein expression profile qualify the cells of the sample (s) as human floorplate mesDA progenitor cells:

80-100%, preferentially 90-100% of the cells of said sample are positive for FOXA2, 80-100%, preferentially 90-100% of the cells of said sample are positive for OTX2, Less than 10%, preferentially less than 5% of the cells of said sample are positive for PAX6, Less than 10%, preferentially less than 5% of the cells of said sample are positive for NKX6.1, and optionally Less than 0.1% of the cells of said sample are positive for OCT3/4, and/or 5-90%, preferentially 5-70% of the cells of said sample are positive for NKX2.1, and/or 10-90% of the cells of said sample are positive for KI-67, and/or 80-100%, preferentially 90-100% of the cells of said sample are positive for IAP, and/or Less than 10%, preferentially less than 5% of the cells of said sample are positive for SOX1.

The cells of said sample reflect the composition of the cells in said cell composition from which the sample has been taken. Therefore, if e.g. the sample taken on day 16 after the differentiation process shows a protein expression profile as indicated above, the cells of the cell composition qualify as human floorplate mesDA progenitor cells and might be transplanted e.g. in a patient in need to be treated for Parkinson Disease. These cells are qualified as floorplate mesDA progenitor cells, that have the potential to integrate into the striatum after transplantation and restore the functions of dopaminergic neurons.

In another embodiment of the invention, a sample or several samples are taken from a cell composition that is expected to comprise human floorplate mesDA progenitor cells. The cells of the cell composition were in-vitro differentiated from human iPS cells to human floorplate mesDA progenitor cells using e.g. the EB based protocol described in example 1.

For monitoring the differentiation status said samples are taken from said cell composition at several time-points, e.g. 4, 6, 8, 11, 14, 16, and/or 18 days after starting the differentiation procedure. The cells of the samples are subdivided and contacted with combinations of the markers described for protein expression profiling of floorplate mesDA differentiated progenitor cells.

E.g. staining of an antibody specific for the antigen FOXA2 coupled to APC, is combined with an antibody specific for IAP coupled to PE and an antibody specific for OTX coupled to FITC. Furthermore PAX6, OCT3/4, KI-67 and NKX2.1, NKX6.1, SOX1 are combined, whereas combined antibodies are conjugated to different fluorophores.

In one embodiment of the invention the cells of the cell composition are in-vitro differentiated from human pluripotent stem cells such as iPS cells or human embryonic stem cells to human floorplate mesDA progenitor cells using e.g. an adherent differentiation protocol described in example 2.

The protein expression profile of the cells is determined as described above after several time points. The cells of said sample reflect the composition of the cells in said cell composition from which the sample has been taken. Therefore, if e.g. the sample taken on day 16 after the differentiation process shows a protein expression profile as described in the present invention, the cells of the cell composition qualify as floorplate mesDA progenitor cells, that have the potential to integrate into the striatum after transplantation and restore the functions of dopaminergic neurons.

In another embodiment of the invention cells of a cell composition were in-vitro differentiated from human ES cells to human floorplate mesDA progenitor cells using e.g. an adherent differentiation protocol described in example 2.

The complete cell composition is contacted with combinations of the markers disclosed herein for protein expression profiling of floorplate mesDA differentiated progenitor cells.

E.g. staining of an antibody specific for the antigen FOXA2 coupled to APC, is combined with an antibody specific for IAP coupled to PE and an antibody specific for OTX coupled to FITC. Furthermore PAX6, KI-67 and NKX2.1, NKX6.1, SOX1 are combined, whereas combined antibodies are conjugated to different fluorophores.

If the staining of the cells of the cell composition results in the protein expression profile as disclosed herein, it is shown that the differentiation protocol allows generation of therapeutically relevant mesDA neurons In one embodiment of the invention the cells of the cell composition are directly reprogrammed from OCT3/4 negative human somatic cells to human floorplate mesDA progenitor cells by methods (protocols) known in the art.

For monitoring the differentiation status said samples are taken from said cell composition at several time-points, e.g. 4, 6, 8, 11, 14, 16, and/or 18 days after starting the differentiation procedure. The cells of the samples are subdivided and contacted with combinations of the markers described for protein expression profiling of floorplate mesDA differentiated progenitor cells.

E.g. staining of an antibody specific for the antigen FOXA2 coupled to APC, is combined with an antibody specific for IAP coupled to PE and an antibody specific for OTX coupled to FITC. Furthermore PAX6, KI-67 and NKX2.1, NKX6.1, SOX1 are combined, whereas combined antibodies are conjugated to different fluorophores.

In another embodiment of invention floorplate mesDA progenitor cells are generated using e.g. an adherent differentiation protocol described in example 2 and analyzed by immunocytochemistry after 16 days of differentiation using antigen binding molecules conjugated to fluorophores specific for the antigens FOXA2, OTX2, PAX6, and NKX6.1.

EXAMPLES

Example 1: Differentiation of Human Embryonic Stem Cells to Floorplate mesDA Progenitor Cells Based on Embryoid Body (EB) Formation and Single Cell Protein Profiling Using Flow Cytometry After 16 Days In Vitro Human embryonic stem cells were differentiated towards floorplate mesDA progenitors cells. The protocol was adapted from Kirkeby et al. 2012, 2013. For differentiation the human embryonic stem cells were harvested with TrypLE (Life Technologies, 12563-029). Single cells were seeded in low attachment plates ($2\times10^6$/2 ml/6 well) to form EBs in DMEM-F12: MACS Neuro (1:1), N2 supplement (1:100; Gibco 17502-48), NeuroBrew-21 w/o vitamin A (1:50; Miltenyi Biotec 130-097-263), 2 mM L-Glutamine. ROCK-Inhibitor (Thiazovivin 2 µM, Miltenyi Biotec 130-104-461) was added for the first two days. On d4, the cells were plated on polyornithine (PO: 15 µg/ml; Sigma P3655), fibronectin (FN: 5 µg/ml; BIOPUR AG 11-50-1104) and laminin (LN: 5 µg/ml; Sigma L20-20) coated plastic ware. From d0 to d9 the following neuralization and patterning factors were present SB431542 (10 µM, Miltenyi Biotec 130-105-336), LDN193189 (100 nM, Miltenyi Biotec 130-103-925), CHIR99021 (0.8 µM, Miltenyi Biotec 130-103-926), hSHH-C24-II (200 ng/ml, Miltenyi Biotec 130-095-727). From d2-d9 Purmorphamine (0.5 µM, Miltenyi Biotec 130-104-465) was added to the medium. On day 11 of differentiation, the cells were dissociated into single cells with TrypLE and replated on dry PO/LN/FN coated plates in droplets of 10,000 cells/µl in MACS Neuro medium, NeuroBrew-21 w/o vitamin A (1:50), BDNF (20 ng/ml; Miltenyi Biotec 130-096-285), GDNF (10 ng/ml; Miltenyi Biotec 130-096-290) and ascorbic acid (200 µM; Sigma A5960).

Single cell protein expression profiling was carried out on day 11 of the differentiation process. Therefore, cells were dissociated into single cells with TrypLE and contacted with antibodies conjugated to fluorophores specific for the antigens FOXA2, OTX2, PAX6, and NKX6.1, thereby labeling the cells of said sample.

In brief, cells were fixed and permeabilized using the FoxP3 buffer set (Miltenyi Biotec 130-093-142). Then, 0.5×10E6 cells were used for staining with FOXA2, OTX2, PAX6, and NKX6.1 specific antibodies coupled to different fluorophors and percentages of positive cells were determined by flow cytometry to analyze if cells showed a protein expression profile that qualifies them as human floorplate mesDA progenitor cells according to the present invention.

Figure 2:
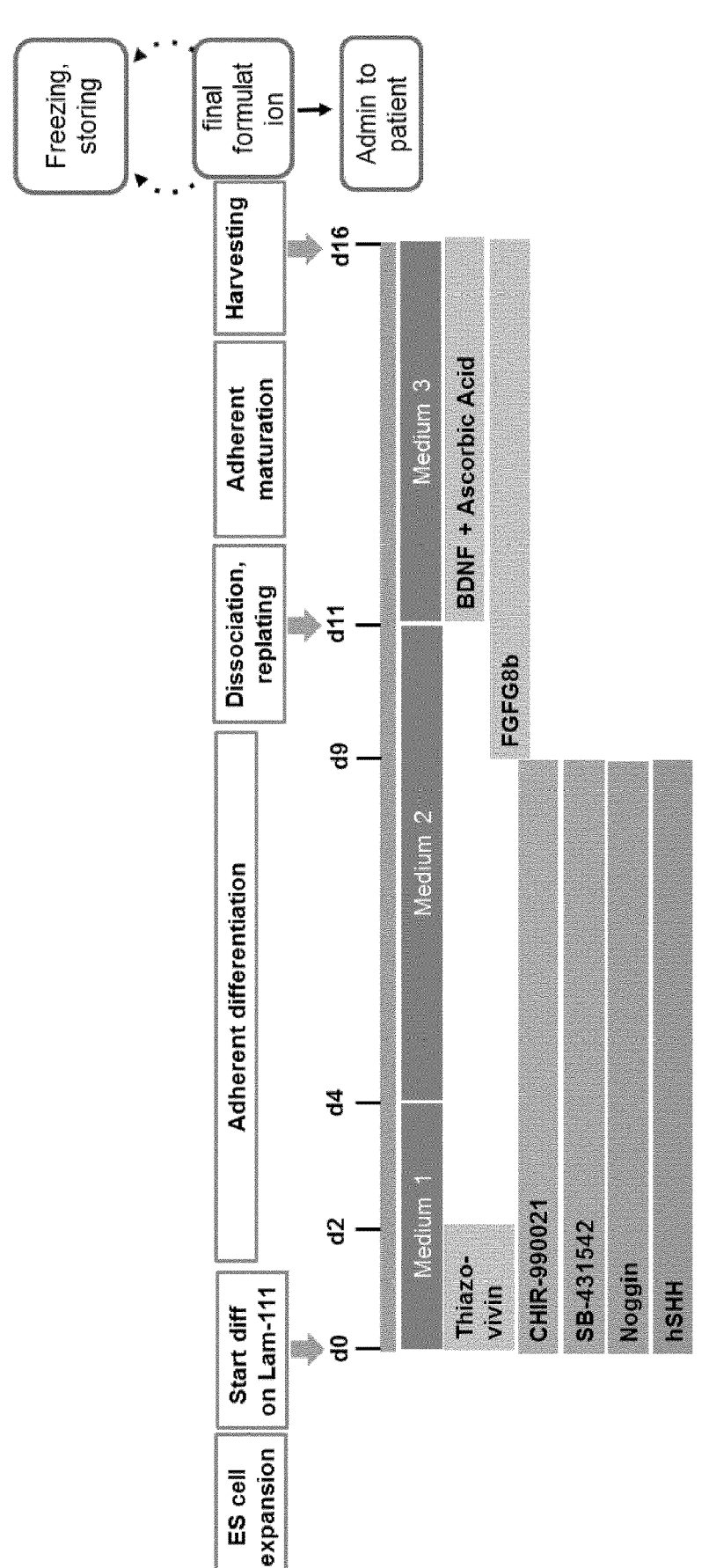
FIG. 2
Schematic differentiation protocol:
Human ES cells and iPS cells are differentiated by defined protocols to floorplate mesDA progenitor cells. Protocols are based on dual SMAD inhibition for neural conversion and regionalization by inhibition of glycogen synthase kinase 3 (GSK3) by CHIR99021 to induce WNT signaling for rostro-caudal patterning and activation of sonic hedgehog (SHH-C24II) for ventralised patterning (Kirkeby, 2012, 2013). Different media are optimized for neural induction (medium 1), neural proliferation (medium 2) and neural differentiation (medium 3).

Example 2: Adherent Differentiation of Human Embryonic Stem Cells to Floorplate Mesencephalic Dopaminergic Progenitor Cells and Single Cell Protein Profiling Using Flow Cytometry After 16 Days In Vitro Human embryonic stem cells (hES cells) were differentiated towards floorplate mesDA progenitors cells. The protocol was adapted from Kirkeby et al. 2012, 2013, whereas the EB based protocol was adapted to a fully adherent cultivation (FIG. 2). For differentiation the hES cells were harvested with TrypLE (Life Technologies, 12563-029). Single cells were seeded at a density of 90,000 cells per 12 well (23684 cells/cm²) on Laminin-111 (Biolamina, LN111) in a neural induction medium, containing DMEM-F12: MACS Neuro (1:1), N2 supplement (1:100; Gibco 17502-48), NeuroBrew-21 w/o vitamin A (1:50; Miltenyi Biotec 130-097-263), 2 mM L-Glutamine (Medium 1). ROCK-Inhibitor (Thiazovivin 2 µM, Miltenyi Biotec 130-104-461) was added for the first two days. On d4, the medium was changed to a neural proliferation medium (Medium 2), that contains DMEM-F12: MACS Neuro (1:1), N2 supplement (1:200), NeuroBrew-21 w/o vitamin A (1:100), and 2 mM L-Glutamine. From d0 to d9 the following neuralization and patterning factors were present: SB431542 (10 µM, Miltenyi Biotec 130-105-336), Noggin (100 ng/ml Miltenyi Biotec 130-103-456), CHIR99021 (0.7 µM, Miltenyi Biotec 130-103-926), hSHH-C24-II (600 ng/ml, Miltenyi Biotec 130-095-727). On day 9 FGF8b (100 ng/ml, Miltenyi Biotec 130-095-740) was added. On day 11 of differentiation, the cells were dissociated into single cells with TrypLE and replated on Laminin-111 coated plates with a density of 800,000 cells/cm² in MACS Neuro medium, NeuroBrew-21 w/o vitamin A (1:50), 2 mM L-glutamine (Medium 3). In addition, BDNF (20 ng/ml; Miltenyi Biotec 130-096-286), and ascorbic acid (200 µM; Sigma A5960) were added (FIG. 2).

Single cell protein expression profiling was carried out on day 16 of the differentiation process. Therefore, cells were dissociated into single cells with TrypLE and contacted with antibodies conjugated to fluorophores specific for the antigens FOXA2, OTX2, PAX6, and NKX6.1 thereby labeling the cells of said sample.

In brief, cells were fixed and permeabilized using the FoxP3 buffer set (Miltenyi Biotec 130-093-142). Then, cells were stained with the following antibodies conjugates, whereas 0.5×10E6 cells were used for each staining:

Anti-FoxA2-APC,

Anti-Otx2-FITC

Anti-Pax6-PE,

Anti-Nkx6.1-AlexaFluor647

Flow analysis showed 92.6% FOXA2, 93.1% OTX2, 0.83% PAX6, and 2.6% NKX6.1, positive cells.

In summary, the cells showed a protein expression profile that qualifies them as human floorplate mesDA progenitor cells according to the present invention (FIG. 3).

Example 3: Adherent Differentiation of Induced Pluripotent Stem Cells to Floorplate Mesencephalic Dopaminergic Progenitor Cells and Single Cell Protein Profiling Using Flow Cytometry After 16 Days In Vitro Induced pluripotent human stem cells (iPS cells) were differentiated towards floorplate mesDA progenitors cells according to the differentiation protocol described in example 2. From d0 to d9 the following neuralization and patterning factors were present SB431542 (10 µM, Miltenyi Biotec 130-105-336), Noggin (100 ng/ml Miltenyi Biotec 130-103-456), CHIR99021 (1 µM, Miltenyi Biotec 130-103-926), hSHH-C24-II (400 ng/ml, Miltenyi Biotec 130-095-727). On day 11 of differentiation, the cells were dissociated into single cells with TrypLE and replated on Laminin-111 coated plates with a density of 800,000 cells/cm$^2$ in MACS Neuro medium, NeuroBrew-21 w/o vitamin A (1:50), 2 mM L-glutamine (Medium 3). In addition, FGF8b (100ng/ml, Miltenyi Biotec 130-095-740), BDNF (20 ng/ml; Miltenyi Biotec 130-096-286), and ascorbic acid (200 µM; Sigma A5960) were added.

Single cell protein expression profiling was carried out on day 16 of the differentiation process. Therefore, cells were dissociated into single cells with TrypLE and contacted with antibodies conjugated to fluorophores specific for the antigens FOXA2, OTX2, PAX6, and NKX6.1 thereby labeling the cells of said sample.

Flow analysis showed 93.8% FOXA2, 94.4% OTX2, 1.3% PAX6, and 1.2% NKX6.1, positive cells.

In summary, the cells showed a protein expression profile that qualifies them as human floorplate mesDA progenitor cells according to the present invention (FIG. 4).

Example 4: Adherent Differentiation of Human Embryonic Stem Cells With Different Concentrations of CHIR and Single Cell Protein Profiling Using Flow Cytometry After 16 Days In Vitro Human embryonic stem cells were differentiated according to the adherent differentiation protocol described in example 2. The patterning factors CHIR99021 (Miltenyi Biotec 130-103-926) and hSHH-C24-II (Miltenyi Biotec 130-095-727) were applied at different concentrations to pattern cells towards a ventral forebrain, a dorsal forebrain and a ventral hindbrain identity.

A Ventral forebrain: CHIR99021: 0 µM, hSHH-C24-II: 800 ng/ml

B Dorsal forebrain: CHIR99021: 0 µM, hSHH-C24-II: 0 ng/ml

C Ventral hindbrain: CHIR99021: 4 µM, hSHH-C24-II: 800 ng/ml

Single cell protein expression profiling was carried out on day 16 of the differentiation process. Therefore, cells were dissociated into single cells with TrypLE, fixed and permeabilized using the FoxP3 buffer set (Miltenyi Biotec 130-093-142). Then cells were subdivided into three sub-sample and contacted with antibodies conjugated to fluorophores specific for the antigens FOXA2, OTX2, PAX6, NKX6.1, OCT3/4, NKX2.1, IAP, KI-67, SOX1, whereas 0.5×10E6 cells were used for each staining.

Figure 1:
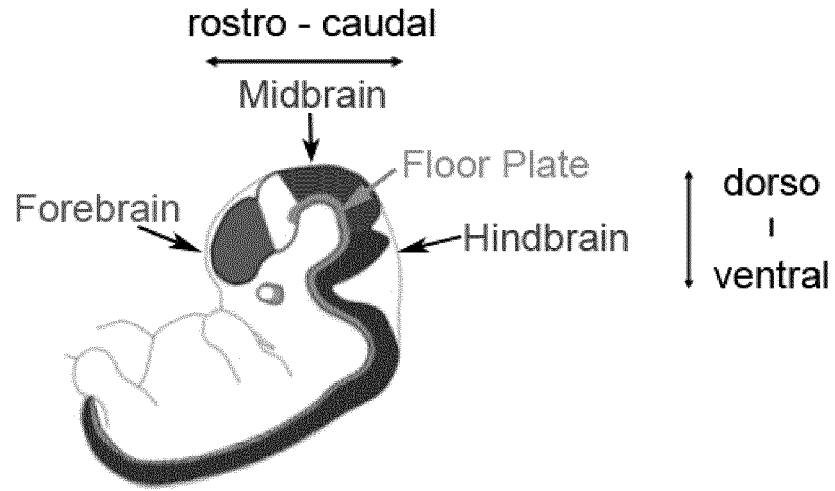
FIG. 1
Schematic drawing and marker expression of a human fetal brain:
The neural tube can be subdivided into different regions along the rostro-caudal axis and the dorso-ventral axis. The most rostral part of the neural tube is called the forebrain, followed by the midbrain and the most caudal part forms the hindbrain. The most ventral part of the neural tube is called the floor plate. Cells of the different brain regions are characterized by specific marker expression (forebrain: PAX6, OTX2, NKX2.1), ventral midbrain: FOXA2, OTX2, NKX2.1, hindbrain: NKX6.1).

The following antibody fluorochromes were combined for simultaneous staining of three antigen binding molecules:

Anti-FoxA2-APC, Anti-Otx2-FITC, Anti-IAP-PE
Anti-Pax6-PE, Anti-Oct3/4-APC, Anti-Ki-67-FITC
Anti-Nkx6.1-AlexaFluor 647, Anti-Nkx2.1-AlexaFluor 488, Anti-Sox1-PE Below 80% FOXA2 expression in the different samples, >10% PAX6 expression in the dorsal forebrain and hindbrain sample, >90% NKX2.1 expression in the ventral forebrain sample, and <80% of OTX2 as well as >10% ofNKX6.1 expression in the ventral hindbrain sample clearly indicates that the cells did not show a floorplate mesDA progenitor cell phenotype and are not qualified for transplantation (FIG. 1, FIG. 5).

Example 5: Adherent Differentiation of Human Embryonic Stem Cells to Floorplate Mesencephalic Dopaminergic Progenitor Cells and Single Cell Protein Profiling Using Flow Cytometry After 4, 8, 11, and 16 Days In Vitro Human embryonic stem cells were differentiated according to the adherent differentiation protocol described in example 2. The patterning factors CHIR99021 (Miltenyi Biotec 130-103-926) and hSHH-C24-II (Miltenyi Biotec 130-095-727) were applied at a concentration of 0.7 µM and 600 ng/ml, respectively.

Single cell protein expression profiling was carried out on day 4, 8, 11, and 16 of the differentiation process. Therefore, cells were dissociated into single cells with TrypLE, fixed and permeabilized using the FoxP3 buffer set (Miltenyi Biotec 130-093-142). Then cells were subdivided into three sub-sample and contacted with antibodies conjugated to fluorophores specific for the antigens FOXA2, OTX2, PAX6, NKX6.1, OCT3/4, NKX2.1, whereas 0.5×10E6 cells were used for each staining.

The following antibody fluorochromes were combined for simultaneous staining of three antigen binding molecules:

Anti-FoxA2-APC, Anti-Otx2-FITC
Anti-Pax6-PE, Anti-Oct3/4-APC
Anti-Nkx6.1-AlexaFluor 647, Anti-Nkx2.1-AlexaFluor 488

Flow cytometric analysis shows that the cells did not resemble an expression profile that qualifies them as floorplate dopaminergic neurons at d4, d8, and d16 of differentiation according to the present invention. Only cells of d11 of the differentiation process showed a protein expression profile that qualifies them as human floorplate mesDA progenitor cells according to the present invention (FIG. 6).

Example 6: Adherent Differentiation of Human Embryonic Stem Cells for Transplantation Studies in Rats Human embryonic stem cells were differentiated according to the adherent differentiation protocol described in example 2. The patterning factors CHIR99021 (Miltenyi Biotec 130-103-926) and hSHH-C24-II (Miltenyi Biotec 130-095-727) were applied at a concentration of 0.7 µM and 600 ng/ml, respectively.

On day 16 of the differentiation process cells were dissociated into single cells with TrypLE. A sample was taken and cells were fixed and permeabilized using the FoxP3 buffer set (Miltenyi Biotec 130-093-142). Then, cells were subdivided into sub-samples and contacted with antibodies conjugated to fluorophores specific for the antigens FOXA2, OTX2, PAX6, NKX6.1, OCT3/4, NKX2.1, IAP, KI-67, SOX1, whereas 0.5×10E6 cells were used for each staining. The following antibody fluorochromes were combined for simultaneous staining of three antigen binding molecules:

Anti-FoxA2-APC, Anti-Otx2-FITC, Anti-IAP-PE
Anti-Pax6-PE, Anti-Oct3/4-APC, Anti-Ki-67-FITC
Anti-Nkx6.1-AlexaFluor 647, Anti-Nkx2.1-AlexaFluor 488, Anti-Sox1-PE A sample of differentiated living cells that showed an expression profile which qualifies them as floorplate dopaminergic neurons and a sample of differentiated living cells that did not resemble an expression profile that qualifies them as floorplate dopaminergic neurons were used for transplantation studies into rats. The first sample was correlated with a good engraftment and a high yield of dopaminergic neurons after transplantation in vivo whereas the second sample resulted in a significantly lower yield of dopaminergic neurons in vivo.

Example 7: Immunocytochemical Analysis of FOXA2, OTX2, NKX6.1, and PAX6 Expression After 16 Days of Differentiation Human embryonic stem cells were differentiated according to the adherent differentiation protocol described in example 2. The patterning factors CHIR99021 (Miltenyi Biotec 130-103-926) and hSHH-C24-II (Miltenyi Biotec 130-095-727) were applied at a concentration of 0.7 μM and 600 ng/ml, respectively.

Then immunocytochemical staining was carried out at day 16 of the differentiation process. Therefore, cells were fixed with 4% paraformaldehyde and permeabilized using 0.2% Triton-X-100. Therefore, 4 sub-sample were contacted with antibodies conjugated to fluorophores specific for the antigens FOXA2, OTX2, PAX6, and NKX6.1.

Immunocytochemical analysis showed that a high percentage of FOXA2 and OTX2 positive cells, whereas cells were PAX6 and NKX6.1 negative (FIG. 7).

REFERENCES

Barker RA1, Barrett J, Mason SL, Björklund A, 2013. Fetal dopaminergic transplantation trials and the future of neural grafting in Parkinson's disease. Lancet Neurol. 2013 Jan;12(1): 84-91.

Grealish S, Diguet E, Kirkeby A, Mattsson B, Heuer A, Bramoulle Y, Van Camp N, Perrier AL, Hantraye P, Björklund A, Parmar M, 2014. Human ESC-derived dopamine neurons show similar preclinical efficacy and potency to fetal neurons when grafted in a rat model of Parkinson's disease. Cell Stem Cell. 2014 Nov 6;15(5): 653-65.

Kefalopoulou Z, Politis M, Piccini P, Mencacci N, Bhatia K, Jahanshahi M, Widner H, Rehncrona S, Brundin P, Björklund A, Lindvall O, Limousin P, Quinn N, Foltynie T, 2014. Long-term clinical outcome of fetal cell transplantation for Parkinson disease: two case reports. JAMA Neurol. 2014 January;71(1): 83-7.

Kriks S, Shim JW, Piao J, Ganat YM, Wakeman DR, Xie Z, Carrillo-Reid L, Auyeung G, Antonacci C, Buch A, Yang L, Beal MF, Surmeier DJ, Kordower JH, Tabar V, Studer L,2012. Dopamine neurons derived from human ES cells efficiently engraft in animal models of Parkinson's disease. Nature. 2011 Nov 6;480(7378): 547-51.

Kirkeby A, Grealish S, Wolf DA, Nelander J, Wood J, Lundblad M, Lindvall O, Parmar M., 2012. Generation of regionally specified neural progenitors and functional neurons from human embryonic stem cells under defined conditions. Cell Rep. 2012 Jun 28;1(6): 703-14. doi: 10.1016/j.celrep.2012.04.009.

Kirkeby A, Nelander J, Parmar M., 2013. Generating regionalized neuronal cells from pluripotency, a step-by-step protocol. Front Cell Neurosci. 2013 Jan 3;6:64. doi: 10.3389/fncel.2012.00064.

Kirkeby A, Nolbrant S, Tiklova K, Heuer A, Kee N, Cardoso T, Ottosson DR, Lelos MJ, Rifes P, Dunnett SB, Grealish S, Perlmann T, Parmar M, 2017. Predictive Markers Guide Differentiation to Improve Graft Outcome in Clinical Translation of hESC-Based Therapy for Parkinson's Disease. Cell Stem Cell. 2017 Jan 5;20(1): 135-148. doi: 10.1016/j.stem.2016.09.004.

Ladewig J, Mertens J, Kesavan J, Doerr J, Poppe D, Glaua F, Herms S, Wernet P, Kögler G, Müller FJ, Koch P, Brüstle O, 2012. Small molecules enable highly efficient neuronal conversion of human fibroblasts. Nature Methods, 9:575-578.

The invention claimed is:

1. A method for obtaining and characterizing a composition of human dopaminergic progenitor cells, the method comprising:

a) differentiating a population of human pluripotent stem cells or progeny thereof into a preparation of neural progenitor cells;

b) maturing the preparation of neural progenitor cells into a cell composition that contains dopaminergic progenitor cells;

c) determining what percentage of cells in the composition expresses each of a panel of markers consisting of FOXA2, OTX2, and PAX6, thereby obtaining a protein expression profile;

whereby the cell composition is characterized as having a desirable phenotype if the cell expression profile is as follows:

80 to 100% of said cells are positive for FOXA2, 80 to 100% of said cells are positive for OTX2, and less than 10% of said cells are positive for PAX6;

wherein the percentage of cells in the composition that express each of said markers is determined by flow cytometry or immunocytochemistry of single cells in the cell composition using antigen binding molecules that are specific for each of the markers.

2. The method of claim 1, wherein the percentage of cells in the composition that express each of said markers is determined by flow cytometry of single cells in the cell composition using fluorophore-conjugated antigen binding molecules that are specific for each of the markers.

3. The method of claim 1, wherein said antigen binding molecules are antibodies or antigen binding fragments thereof.

4. The method of claim 1, wherein said human pluripotent stem cells are induced pluripotent stem (iPS) cells or human embryonic stem cells.

5. The method of claim 1, wherein step (a) comprises inhibiting glycogen synthase kinase 3 (GSK3) and activating sonic hedge hog (SHH) signaling in an adherent culture of the stem cells or progeny.

6. The method of claim 5, wherein the adherent culture in step (a) is done in a medium comprising CHIR99021 and SHH protein.

7. The method of claim 1, wherein step (b) comprises culturing the preparation of neural progenitor cells in a medium comprising a plurality of maturation factors selected from bone derived neurotrophic factor (BDNF), glial cell derived neurotrophic factor (GDNF), and fibroblast growth factor 8b (FGF8b).

8. A kit for analyzing the protein expression profile of a preparation of dopaminergic progenitor cells to determine if cells in the preparation have a desirable phenotype, wherein the kit comprises a panel of antigen binding molecules that consists of antibody binding molecules specific for each of FOXA2, OTX2, and PAX6, optionally in combination with other reagents, wherein the kit is configured and the antigen binding molecules are formulated whereby a user of the kit may determine on a single cell basis the percentage of cells in said preparation of neural progenitor cells that express each of said markers, thereby obtaining said protein expression profile.

9. The kit according to claim 8, wherein said antigen binding molecules are antibodies or antigen binding fragments thereof.

10. The kit according to claim 8, wherein said antigen binding molecules are conjugated to fluorophores.

11. The kit according to claim 8, wherein said antigen binding molecules are formulated and configured to determine said protein expression profile by flow cytometry.

12. A method for characterizing a cell composition using the kit of claim 8, comprising:

contacting cells from said cell composition with each of the antibody binding molecules contained in the kit; and consequently, determining whether cells in the composition are positive or negative for FOXA2, OTX2, and PAX6.

13. The method of claim 12, wherein the determining is done by flow cytometry.

14. A kit for analyzing the protein expression profile of a preparation of dopaminergic progenitor cells to determine if cells in the preparation have a desirable phenotype, wherein the kit comprises a panel of antigen binding molecules that consists of antibody binding molecules specific for the three positives markers FOXA2, OTX2, and NKX2. 1 and for the three negative markers OCT3/4, PAX6, and SOX1, optionally in combination with other reagents, wherein the kit is configured and the antigen binding molecules are formulated whereby a user of the kit may determine on a single cell basis the percentage of cells in said preparation of neural progenitor cells that express each of said markers, thereby obtaining said protein expression profile.

15. A method for characterizing a cell composition using the kit of claim 14, comprising:

contacting cells from said cell composition with each of the antibody binding molecules contained in the kit; and consequently, determining whether cells in the composition are positive or negative for a plurality of markers selected from FOXA2, OTX2, NKX2.1, OCT3/4, PAX6, and SOX1.

16. The kit according to claim 14, wherein said antigen binding molecules are antibodies or antigen binding fragments thereof.

17. The kit according to claim 14, wherein said antigen binding molecules are conjugated to fluorophores.

18. The kit according to claim 14, wherein said antigen binding molecules are formulated and configured to determine said protein expression profile by flow cytometry.

\* \* \* \* \*